US010321935B2

(12) United States Patent
Yaari

(10) Patent No.: US 10,321,935 B2
(45) Date of Patent: Jun. 18, 2019

(54) DEVICE FOR TREATING SHOULDER DYSTOCIA

(71) Applicant: Abraham J. Yaari, Zichron Yaacov (IL)

(72) Inventor: Abraham J. Yaari, Zichron Yaacov (IL)

(73) Assignee: Fetalease Ltd., Zichron Yaacov (IL)

( * ) Notice: Subject to any disclaimer, the term of this patent is extended or adjusted under 35 U.S.C. 154(b) by 327 days.

(21) Appl. No.: 15/289,135

(22) Filed: Oct. 8, 2016

(65) Prior Publication Data

US 2017/0020568 A1    Jan. 26, 2017

Related U.S. Application Data

(62) Division of application No. 14/088,413, filed on Nov. 24, 2013, now Pat. No. 9,474,549.

(60) Provisional application No. 61/735,031, filed on Dec. 9, 2012.

(51) Int. Cl.
*A61B 17/00* (2006.01)
*A61B 17/42* (2006.01)
*A61B 17/44* (2006.01)

(52) U.S. Cl.
CPC ............ *A61B 17/442* (2013.01); *A61B 17/42* (2013.01); *A61B 2017/00849* (2013.01)

(58) Field of Classification Search
CPC ........ A61B 17/42; A61B 17/44; A61B 17/442
USPC ........................................................ 606/122
See application file for complete search history.

(56) References Cited

U.S. PATENT DOCUMENTS

| 13,453 | A | * | 8/1855 | Buffum | ................. A61B 17/44 606/122 |
| 713,166 | A | | 11/1902 | Cyr | |
| 2,842,134 | A | | 7/1958 | Post | |
| 4,597,391 | A | * | 7/1986 | Janko | ................. A61B 17/442 606/122 |
| 4,602,623 | A | | 7/1986 | Cherkassky | |
| 5,318,573 | A | * | 6/1994 | Alexander | ........... A61B 17/442 606/1 |
| 5,593,413 | A | | 1/1997 | Alexander | |
| 5,803,926 | A | | 9/1998 | Neward | |
| 5,849,017 | A | * | 12/1998 | Reynolds | ............... A61B 17/44 606/122 |
| 6,398,790 | B1 | | 6/2002 | Alexander | |
| 2007/0198027 | A1 | | 8/2007 | Morch | |
| 2013/0289577 | A1 | | 10/2013 | Berhane | |

OTHER PUBLICATIONS

PCT/US2013/071552 International Search Report (dated Nov. 24, 2013).

* cited by examiner

*Primary Examiner* — Kristen Matter
(74) *Attorney, Agent, or Firm* — Neil D. Gershon

(57) ABSTRACT

A surgical device for treating shoulder dystocia having a first arm having a proximal portion, a distal portion and a first curved surface, a second arm having a proximal portion, a distal portion and a second curved surface and a shoulder engagement section positioned at least between the distal portion of the first and second arms and connecting the first and second arms. The engagement section has an atraumatic surface and is configured to contact and press down on the baby to reposition the baby upon manipulation of the first and second arms.

18 Claims, 14 Drawing Sheets

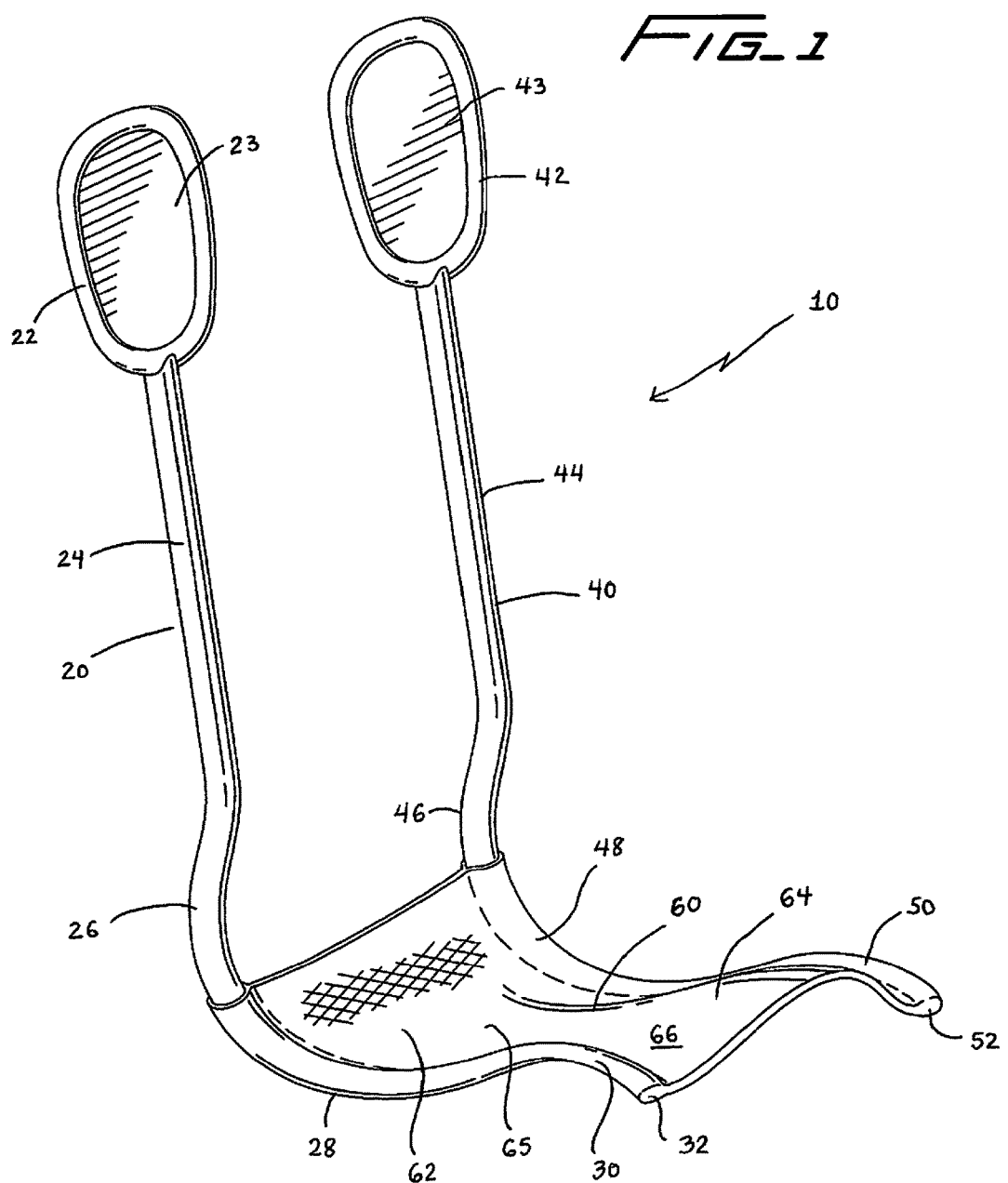

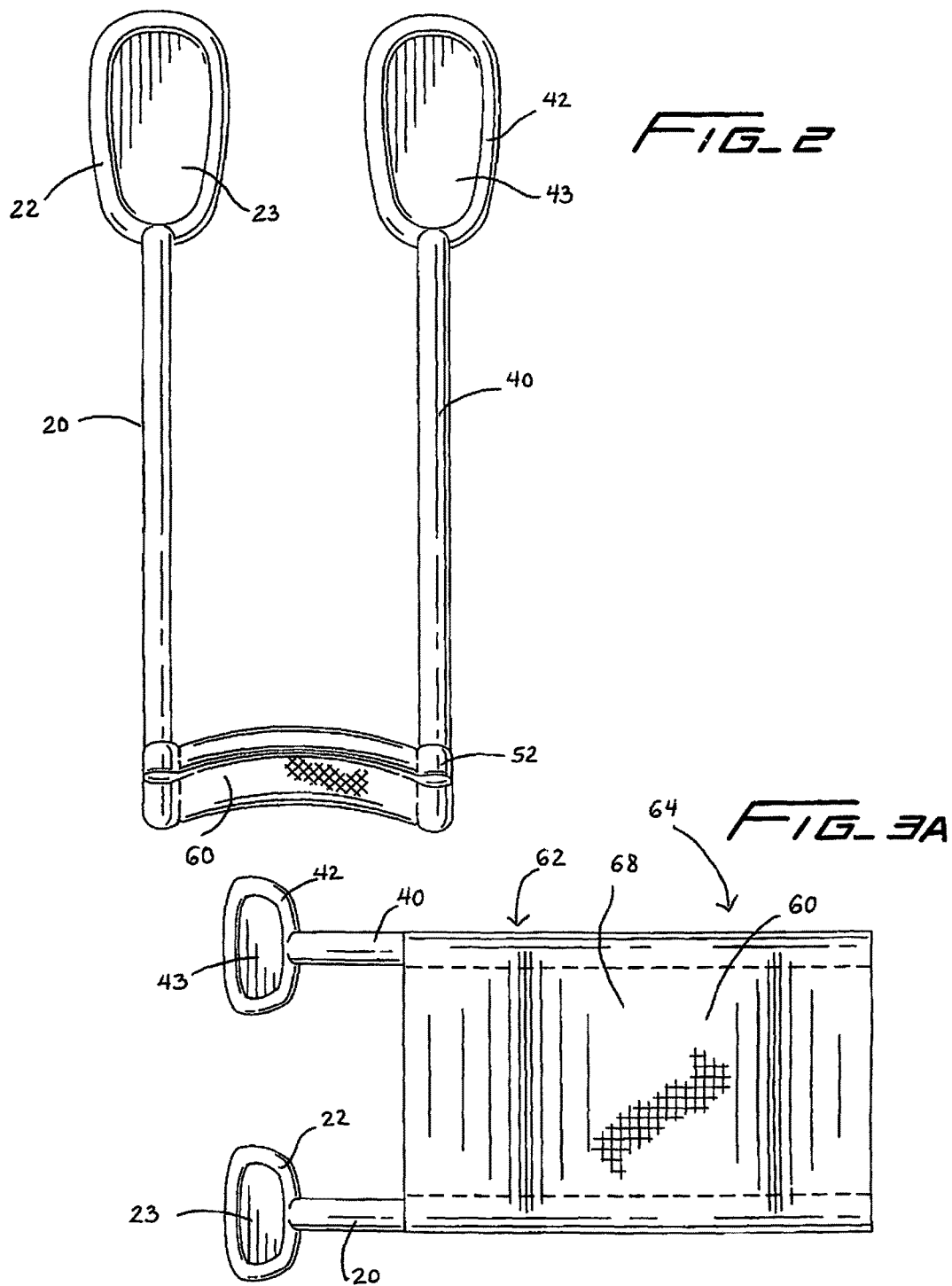

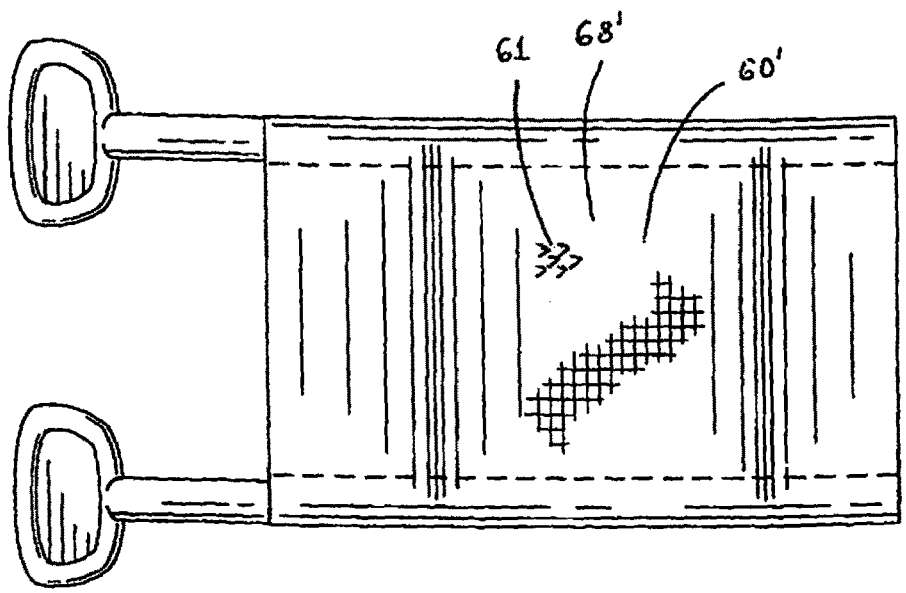
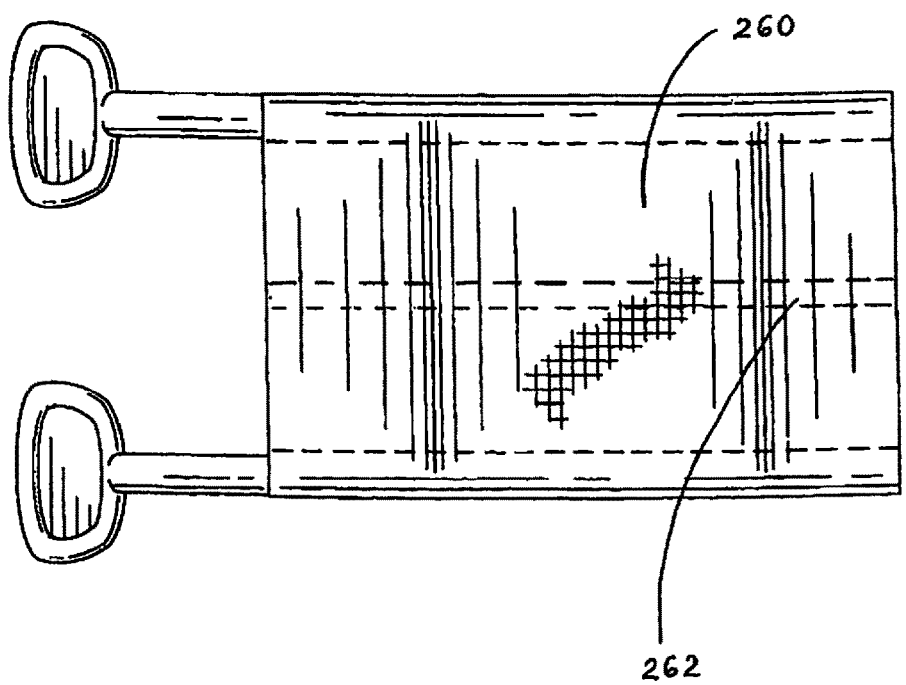

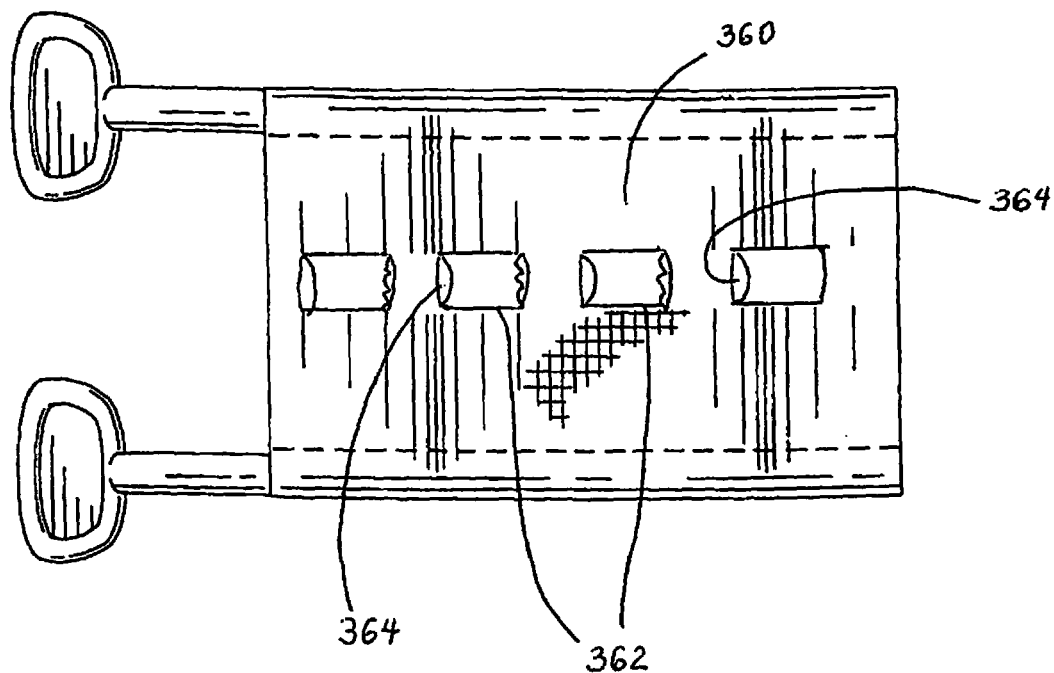

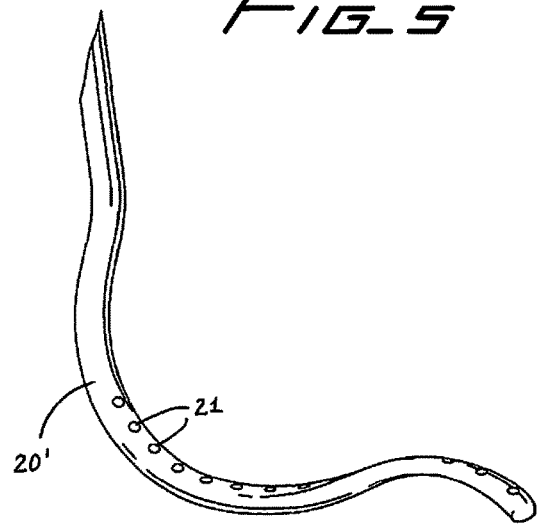
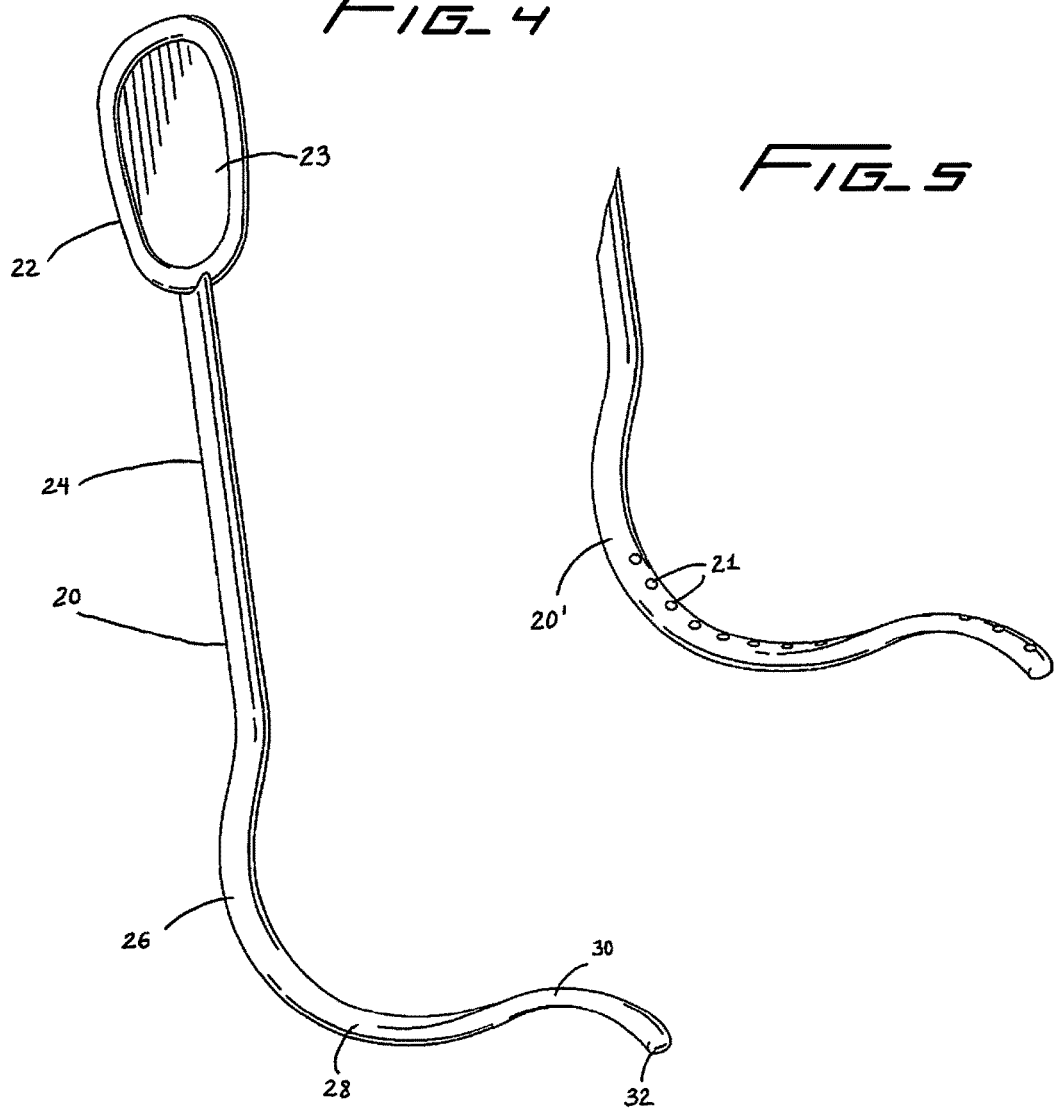
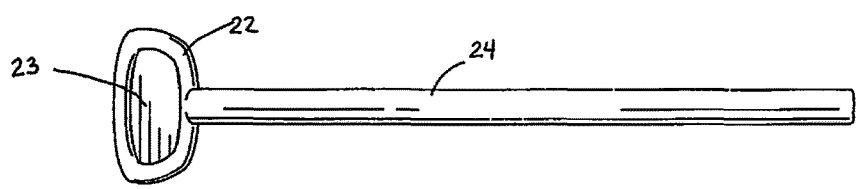

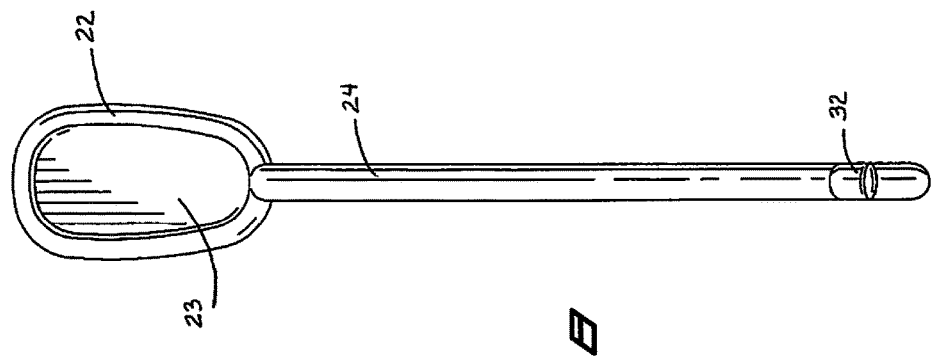
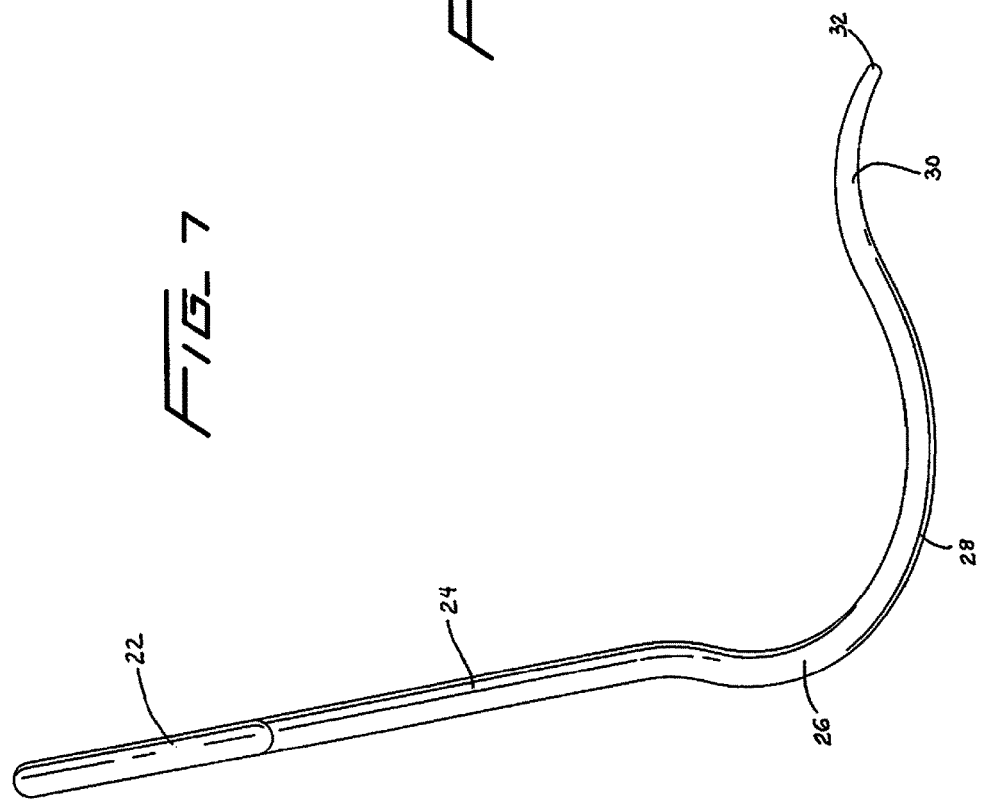

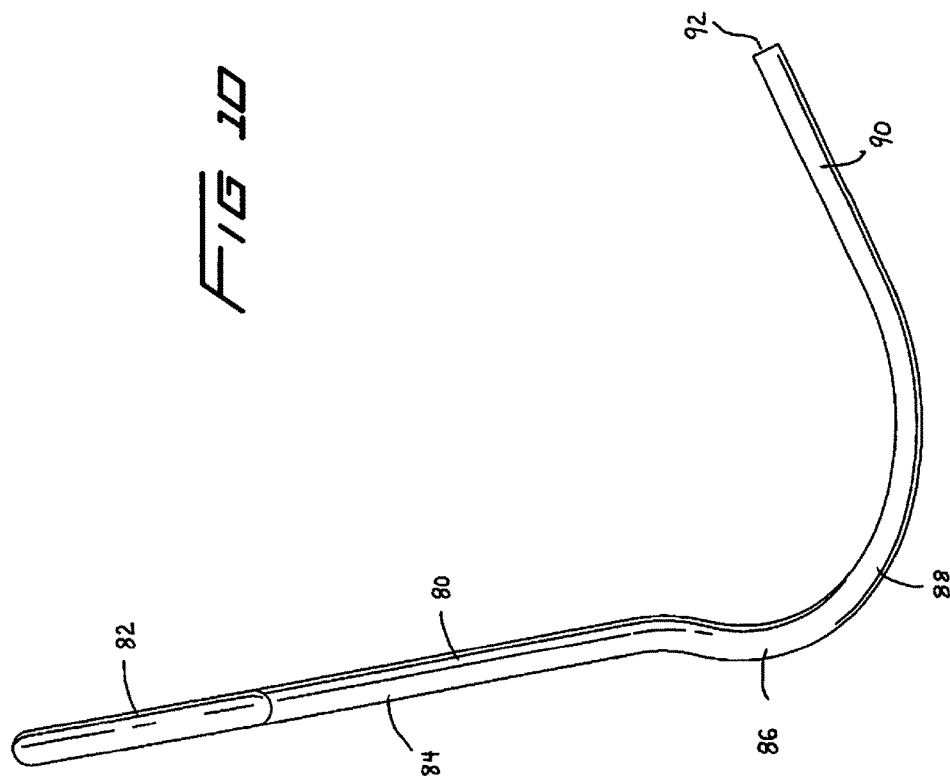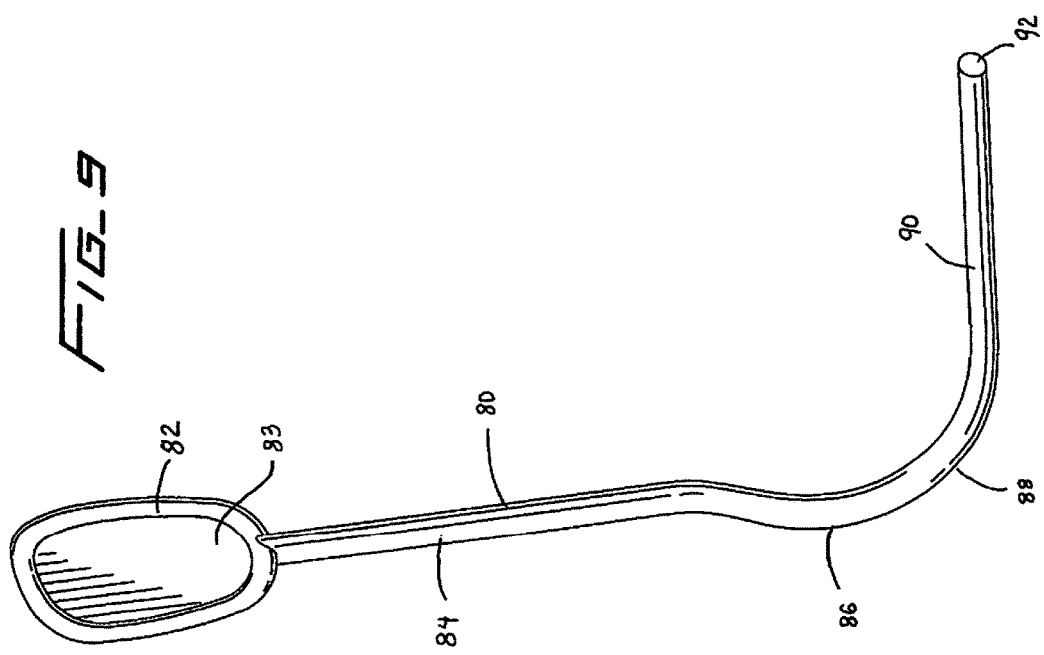

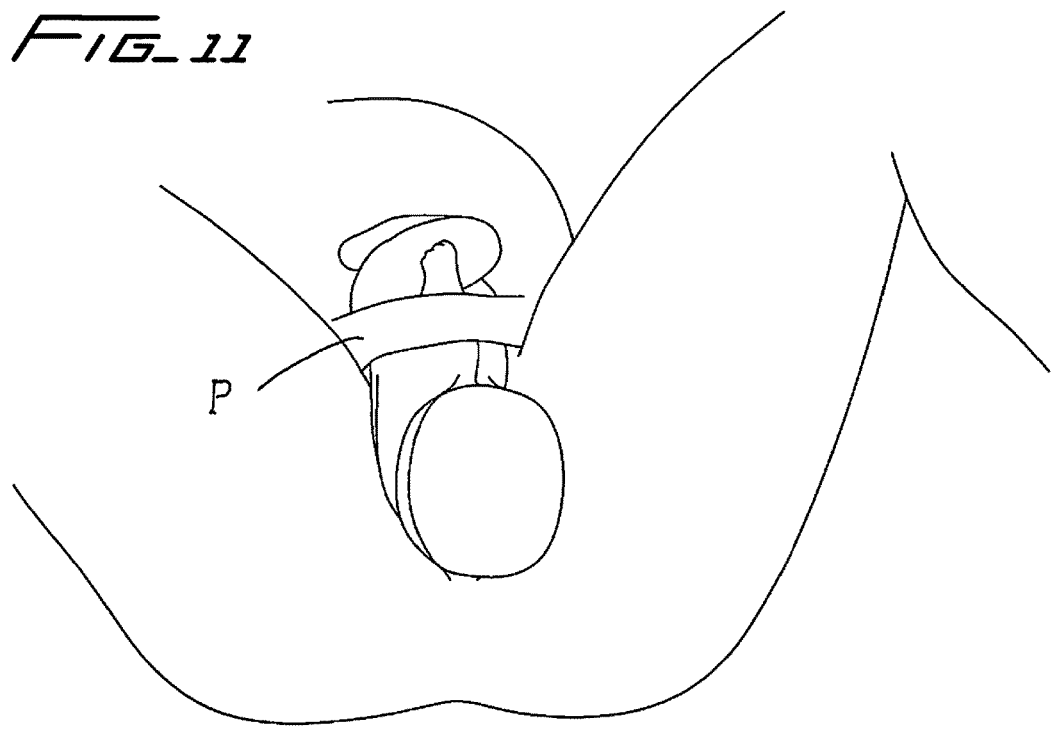
FIG_11
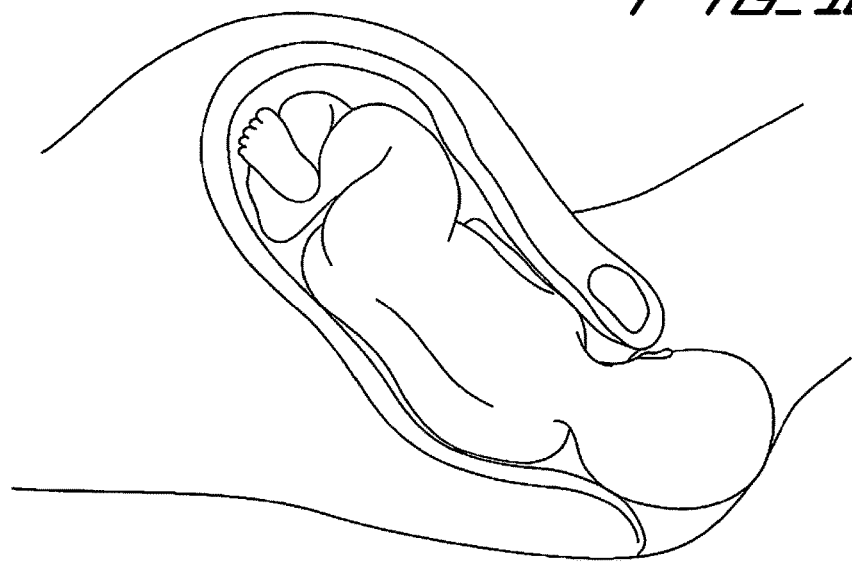
FIG_12

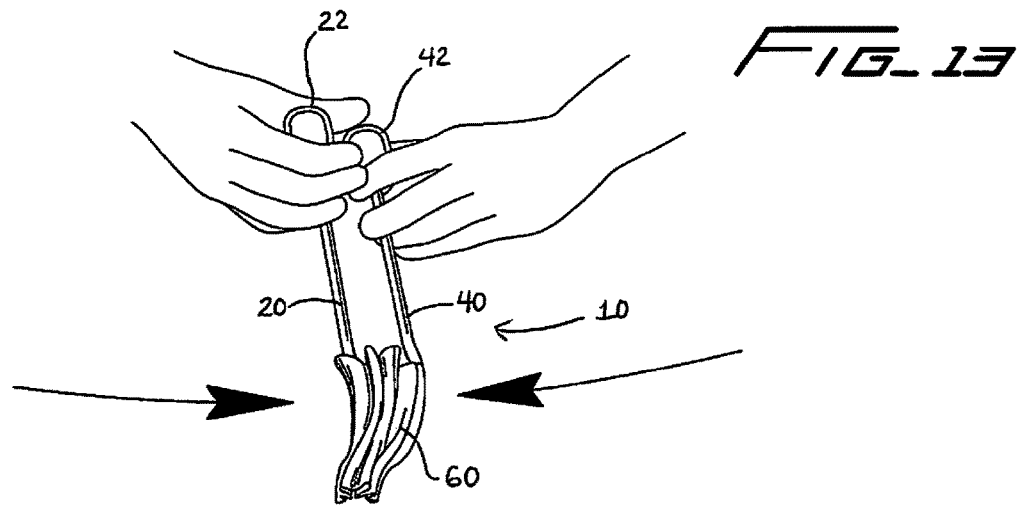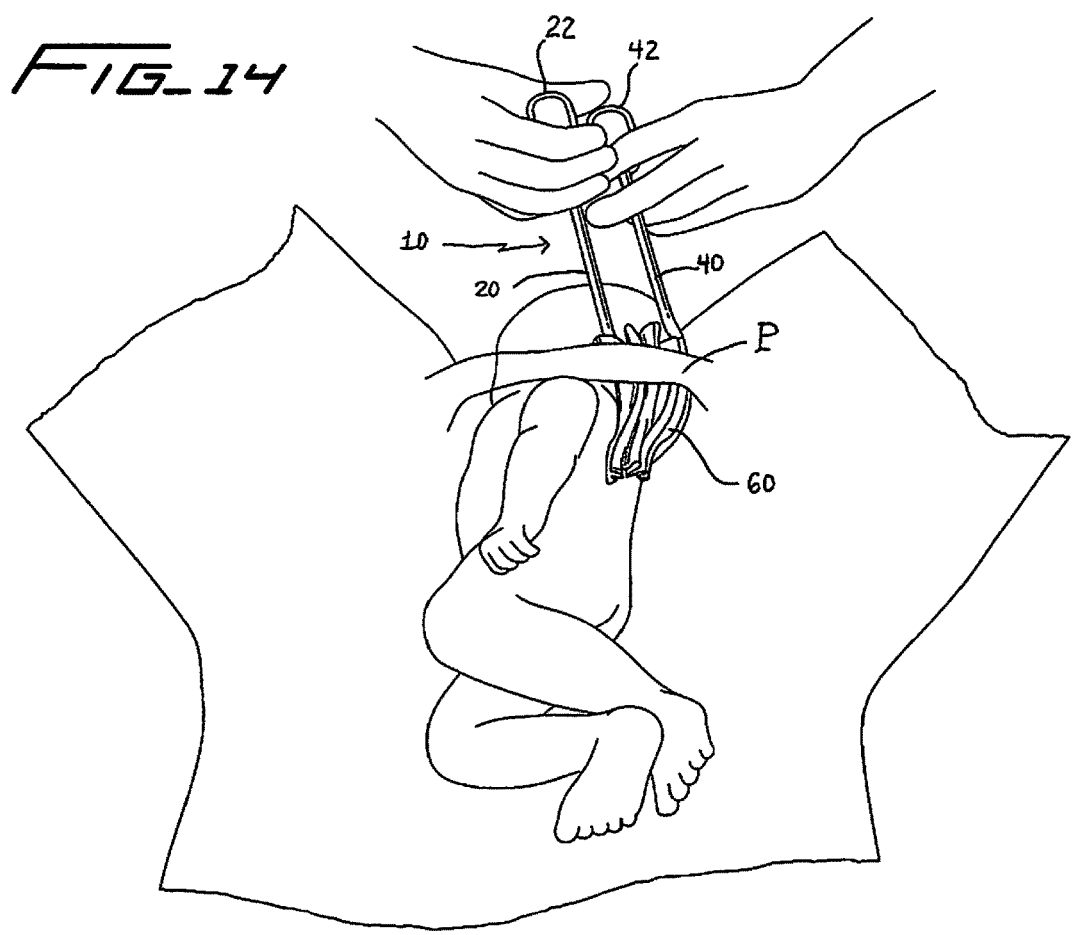

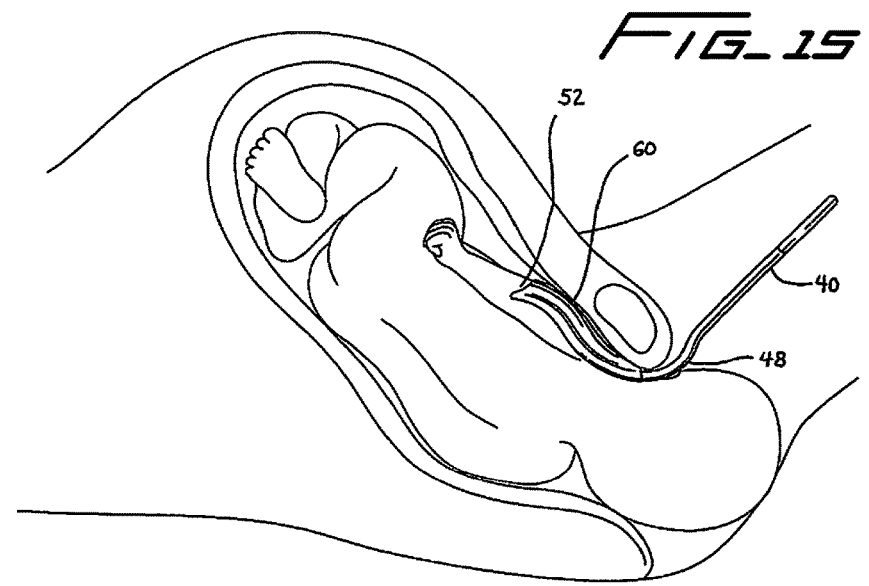
FIG_15
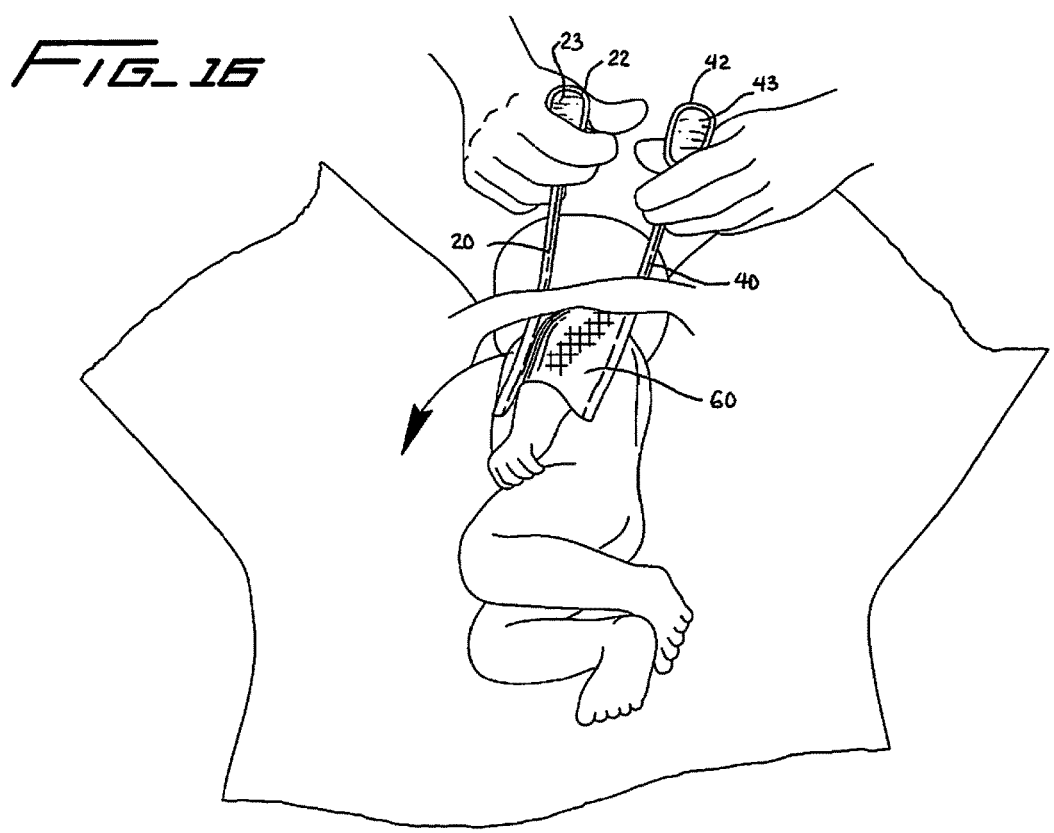
FIG_16

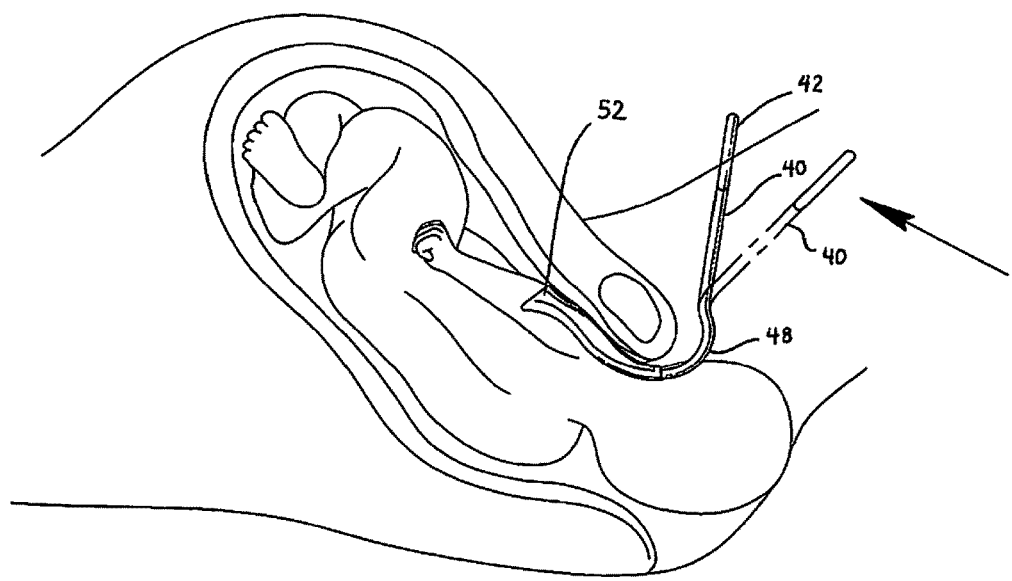
FIG_17
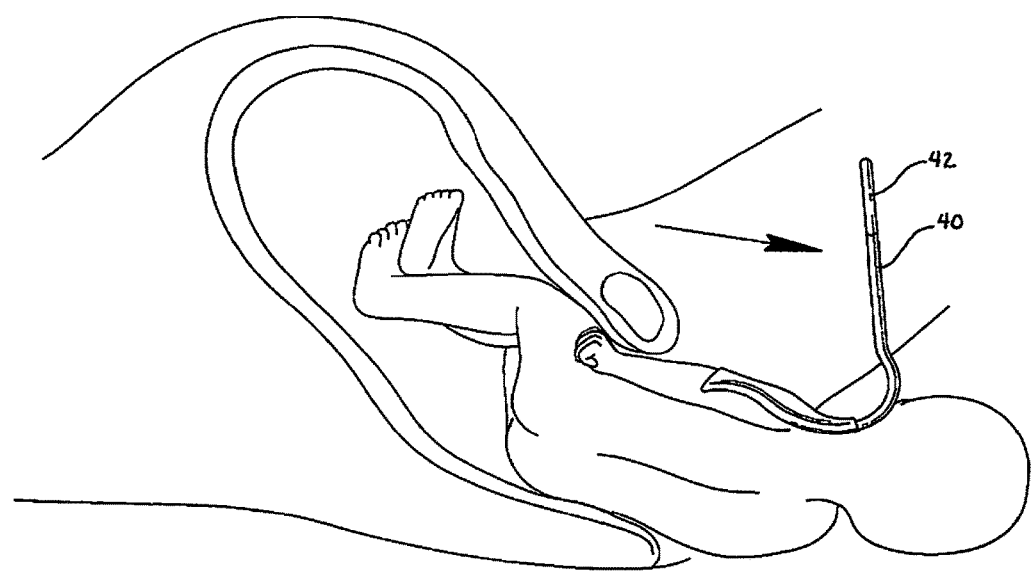
FIG_18

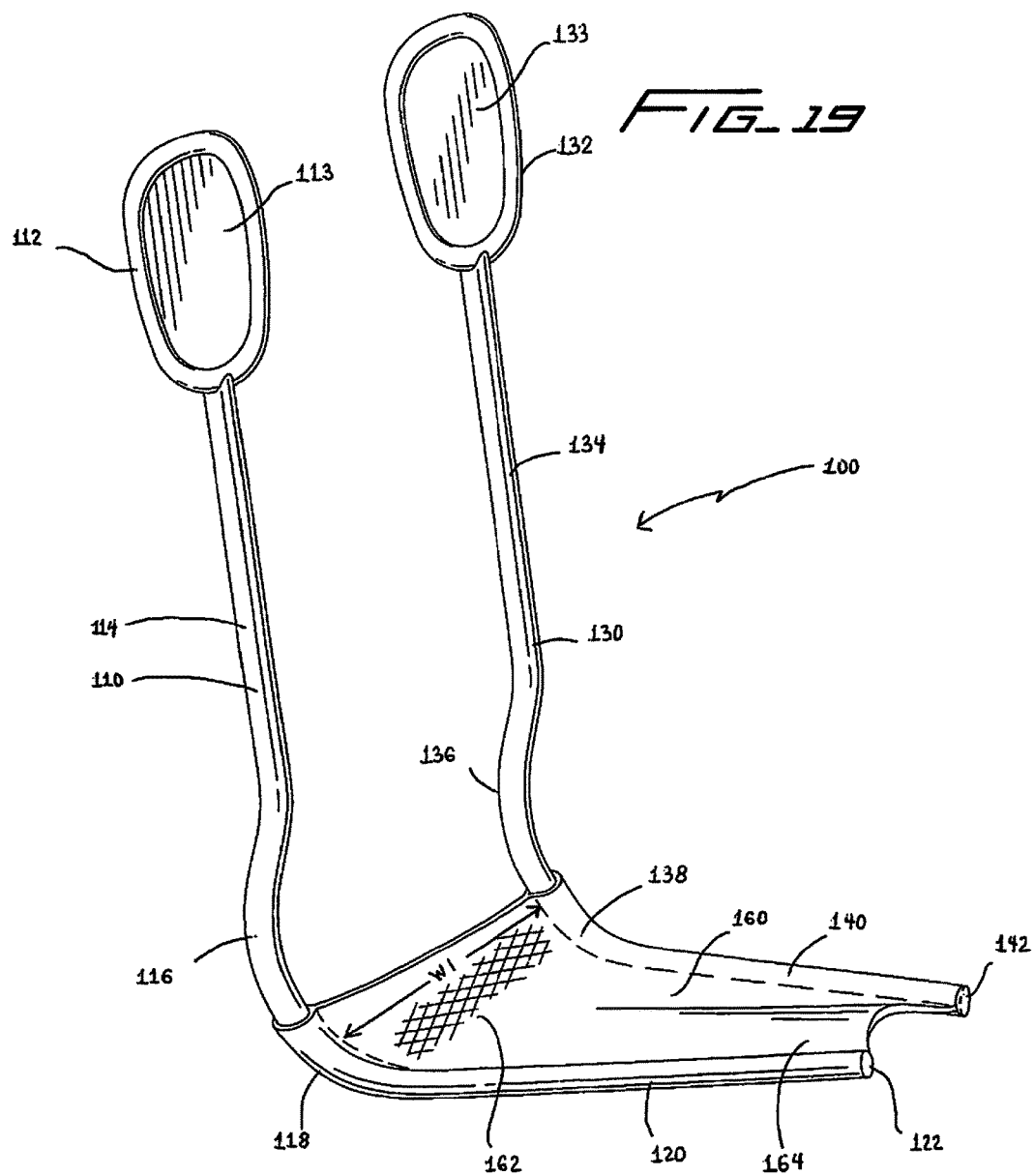

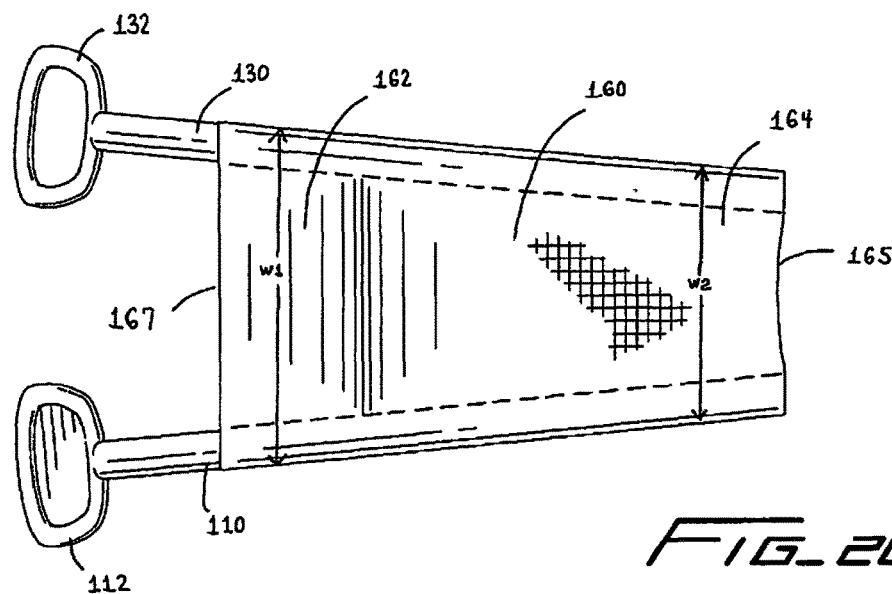
FIG_20
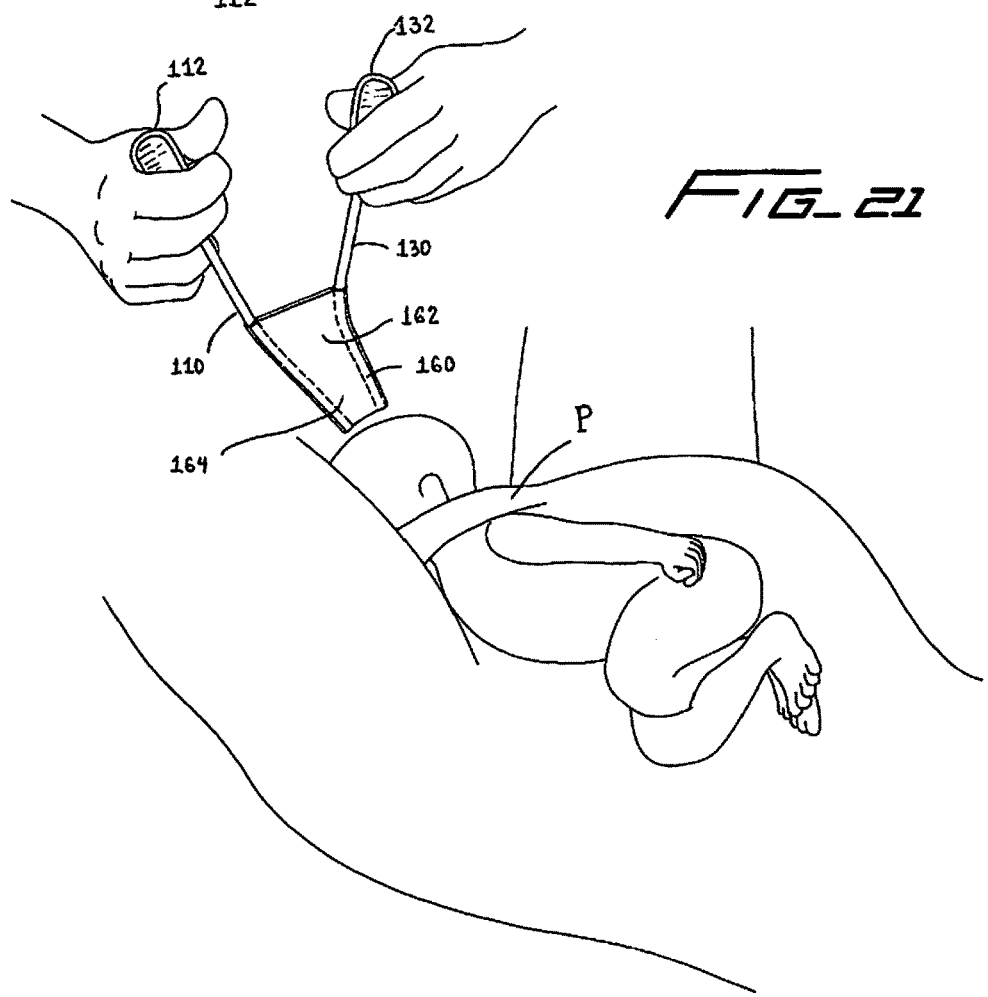
FIG_21

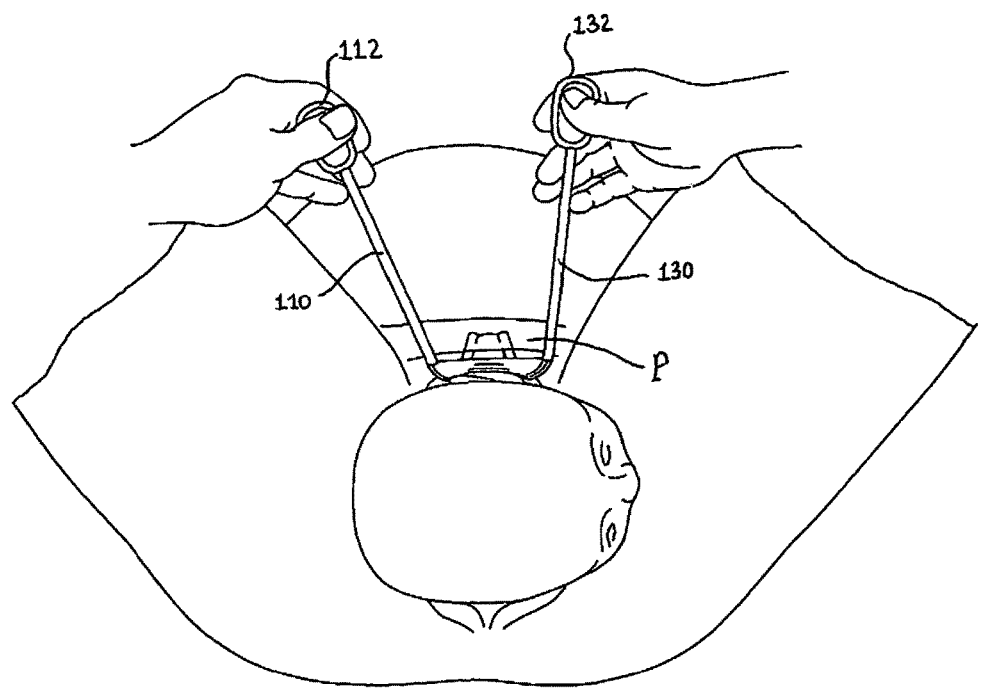
FIG_22
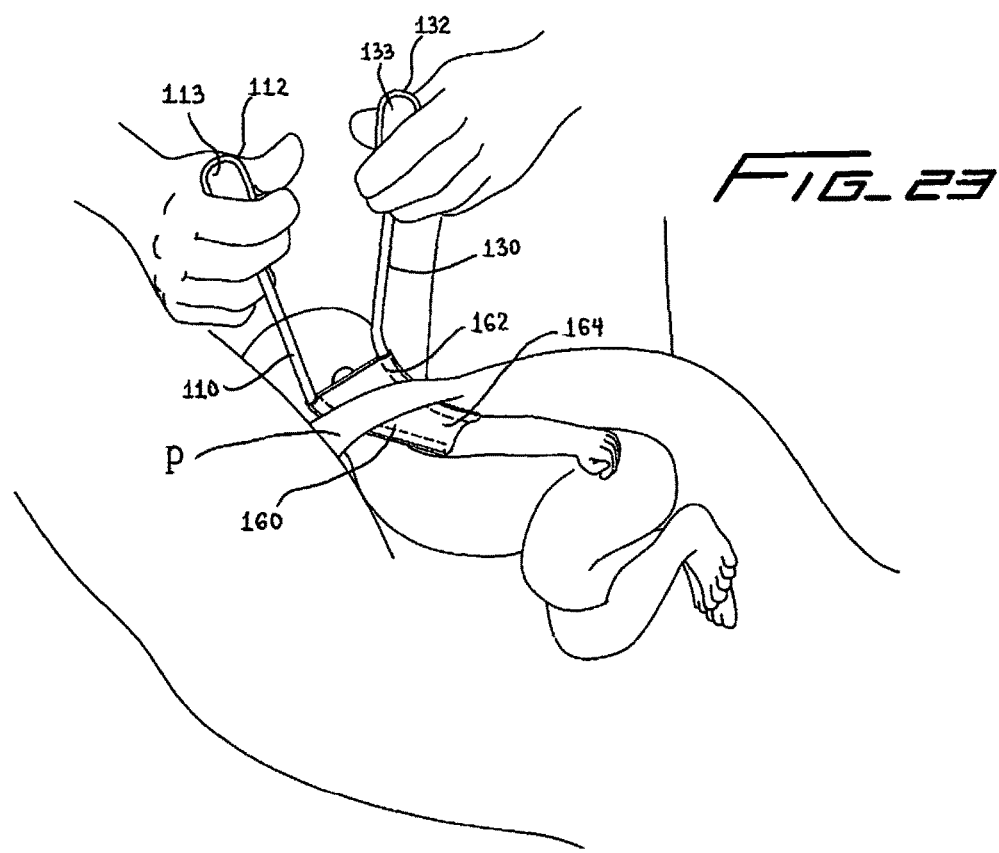
FIG_23

DEVICE FOR TREATING SHOULDER DYSTOCIA

This application is a divisional of application Ser. No. 14/088,413, filed Nov. 24, 2013, which claims priority from provisional application 61/735,031, filed Dec. 9, 2012. The entire contents of each of these applications are incorporated herein by reference.

BACKGROUND

Technical Field

This application relates to a device to assist the surgeon in delivery of a baby and more particularly to a device for delivery of the fetal shoulder in the case of shoulder dystocia.

Background of Related Art

Shoulder dystocia is a condition whereby after delivery of the head of the baby, the anterior shoulder of the baby cannot pass below the pubic symphysis. This creates an obstetric emergency as the baby's life is endangered if not delivered because of compression of the umbilical cord within the birth canal. Additionally, shoulder dystocia can cause several types of injury to the baby as a result of the forces of labor, e.g., maternal pushing acting on the baby, the surgeon's pulling on the fetal head or the surgeon's maneuvers undertaken to free the shoulder for delivery. There are various maneuvers currently being utilized to handle shoulder dystocia, with varying degrees of success and varying risk of causing temporary or permanent injury.

The incidence of shoulder dystocia is increasing as a result of the increase in the average birth weight of babies. The increase in birth weight is due in part to the rise in adult obesity and gestational diabetes as well as the increase in the caloric intake during pregnancy.

Consequently, as the size of babies continues to increase, the incidence of shoulder dystocia has likewise been increasing. Therefore, the need exists to improve delivery of the baby in cases of, or anticipated cases of, shoulder dystocia to reduce the chances of injuring the baby and reduce the incidences of associated morbidity and mortality.

SUMMARY

The present invention advantageously provides a device and method to deliver a baby in the case of shoulder dystocia. The device is inserted into the pelvis below the pubic symphysis and manipulated by the surgeon to free the baby's shoulder from under the pubic symphysis to allow delivery. Alternatively, the device is inserted below the posterior shoulder of the baby to allow rotation of the baby. The present invention also provides a method of freeing the baby's shoulder to deliver the baby in the case of shoulder dystocia. Several embodiments of the device are disclosed herein which can achieve the foregoing. The device and method of the present invention can also be used to prevent the entrapment of the fetal shoulder before it occurs if such an event is anticipated.

In accordance with one aspect of the present invention, a surgical device is provided for treating shoulder dystocia comprising a first arm having a proximal portion, a distal portion, and a first curved surface, a second arm having a proximal portion, a distal portion, and a second curved surface, and a shoulder engagement section positioned at least between the distal portion of the first and second arms and connecting the first and second arms. The engagement section has an atraumatic surface and is configured to contact and press down on a baby to reposition the baby upon manipulation of the first and second arms.

In some embodiments, the engagement section comprises a first section and a second section, wherein the second section is more flexible (less rigid) than the first section and is positioned proximal of the first section. In some embodiments, the first and second sections are composed of the same material; in other embodiments, the first and second sections are composed of a different material. The engagement section can be composed of a variety of materials.

In some embodiments, a distal section of the engagement section has a first width less than a second width of a proximal section of the engagement section so that the distal section is less flexible than the proximal section. The engagement section can be substantially trapezoidal in shape in some embodiments.

The first and second arms can have handle portions, and the handle portions can include a solid surface.

In some embodiments, the first arm includes a third curved surface distal of the first curved surface and the second arm includes a fourth curved surface distal of the second curved surface, the second and fourth curved surfaces providing a curved distal end of the first and second arms.

In some embodiments, a lower surface of the engagement section can have a non-smooth surface to enhance gripping. In some embodiments, the engagement section can include a reinforcement strip. In some embodiments, the engagement section can include one or more pockets to receive an instrument to aid insertion.

The present invention also provides in accordance with another aspect a surgical device for treating shoulder dystocia by moving a baby away from a maternal pubic arch to free a shoulder of the baby to allow delivery. The device comprises a first arm having a proximal portion, a distal portion, and a first curved surface and is configured to be inserted between a baby and the pubic arch. A second arm has a proximal portion, a distal portion, and a second curved surface and is configured to be inserted between a baby and the pubic arch. A shoulder engagement section is positioned at least between a distal region of the first and second arms and connects the first and second arms. The engagement section is configured for insertion between the baby and the pubic arch and has an atraumatic surface for contacting the baby and is configured to contact and press down on a shoulder or chest of the baby to move the baby away from the pubic arch to free the baby's shoulder from the pubic arch to enable delivery of the baby, wherein such pressure on the baby is effected by movement of the arms.

In some embodiments, a distal section of the engagement section is less flexible than a proximal section of the engagement section. In some embodiments, the engagement section has a first width at a distal section and a second width at a proximal section, wherein the first width is less than the second width to thereby provide a less flexible distal section.

In some embodiments, the first arm includes a third curved surface distal of the first curved surface and the second arm includes a fourth curved surface distal of the second curved surface, the second and fourth curved surfaces providing a curved distal end of the first and second arms.

The present invention also provides in accordance with another aspect a method of treating shoulder dystopia comprising the steps of:

providing a device having first and second arms and an engagement section extending between the arms;

inserting the device into a birth canal adjacent the baby; and manipulating the arms so the engagement section applies a force on the baby to free a shoulder of the baby from the pubic arch for delivery.

The method may further comprise the step of inserting the arms in a first position where they are closer to one another and subsequently moving the arms away from each other so they are further apart. In some embodiments, such movement tightens the engagement section. In some embodiments, the method can include the step of rotating the first and second arms to rotate the baby to an oblique position to a diameter of the pelvis. The method may further include the step of manipulating the arms to move distal ends of the arms away from each other after insertion of the arms under the pubic arch.

In some embodiments, the engagement section has a distal section less flexible than a proximal section and the arms are delivered in a spread position.

In some embodiments, manipulating of the arms applies a downward force on one or both of the baby's shoulder and chest.

In some embodiments, the step of inserting the first and second arms includes inserting the arms (and engagement section) directly between the baby's shoulder and the pubic arch. In other embodiments, the step of inserting the first and second arms includes first inserting the arms (and engagement section) in an unspread position along a side of a neck and back of the baby and subsequently maneuvering the engagement section with the arms in the unspread position so the engagement section contacts the shoulder of the baby. In some embodiment, the step of inserting the first and second arms includes the step of inserting the arms (and engagement section) under the posterior shoulder of the baby.

BRIEF DESCRIPTION OF THE DRAWINGS

Preferred embodiment(s) of the present disclosure are described herein with reference to the drawings wherein:

FIG. 1 is a perspective view of a first embodiment of the device of the present invention shown in the open (spread) position;

FIG. 2 is a front view of the device of FIG. 1;

FIG. 3A is a bottom view of the device of FIG. 1;

FIG. 3B is a bottom view similar to FIG. 3A showing an alternate embodiment having an engagement section with a plurality of projections;

FIG. 3C is a bottom view similar to FIG. 3A showing another alternate embodiment having an engagement section with a reinforcement strip;

FIG. 3D is a bottom view similar to FIG. 3A showing another alternate embodiment having an engagement section with a plurality of pockets;

FIG. 4 is perspective view of one of the arms of the device of FIG. 1;

FIG. 5 is a perspective view of a distal portion of one of the arms of a device in accordance with an alternate embodiment of the device of the present invention;

FIGS. 6, 7 and 8 are bottom, side and front views, respectively, of the device of FIG. 1;

FIG. 9 is a perspective view of an alternate embodiment of the device of the present invention showing one of the arms;

FIG. 10 is a side view of the arm of FIG. 9;

FIGS. 11-18 illustrate method steps for delivery of a baby in the case of shoulder dystocia utilizing the device of FIG. 1 wherein:

FIG. 11 is a front view illustrating the baby's shoulder blocked by the pubic symphysis;

FIG. 12 is a side view of the position of the baby of FIG. 11 showing blockage of the shoulder;

FIG. 13 illustrates the surgeon holding the device of FIG. 1 in the closed (unspread) position;

FIG. 14 illustrates the device of FIG. 1 inserted underneath the pubic arch in the closed (unspread) position to access the baby's shoulder;

FIG. 15 is a side view showing the arms of the device of FIG. 1 conforming to the anatomy of the baby with the engagement section positioned over the baby's shoulder;

FIG. 16 illustrates the device of FIG. 1 being moved to the open (spread) position to spread the engagement material spanning the arms;

FIG. 17 is a side view corresponding to the position of FIG. 16 and showing movement of the arms (in phantom) of the device to press down on the baby's shoulder to dislodge it from the pubic arch; and FIG. 18 illustrates delivery of the baby as the shoulder is freed from blockage by the pubic arch by the device of FIG. 1.

FIG. 19 is a perspective view of another alternate embodiment of the device of the present invention;

FIG. 20 is a top view of the device of FIG. 19;

FIGS. 21-23 illustrate method steps for delivery of a baby in case of shoulder dystocia utilizing the device of FIG. 19 wherein FIG. 21 illustrates the surgeon holding the device of FIG. 19 in the unspread position prior to insertion;

FIG. 22 is a front view illustrating the device of FIG. 19 being inserted underneath the pubic arch to access and engage the baby's shoulder; and FIG. 23 is a side view showing the engagement material of the device in contact with the baby's shoulder.

DETAILED DESCRIPTION OF PREFERRED EMBODIMENTS

Referring now in detail to the drawings wherein like reference numerals identify similar or like components throughout the several views, various embodiments of the delivery device of the present invention are illustrated. The devices are designed to deliver a baby in cases of anticipated or actual shoulder dystocia. As described above, in cases of shoulder dystopia, the baby's head is delivered but the shoulder is engaged with the pubic arch, thus blocking delivery. The device of the present invention, as described in detail below, is placed in the birth canal, under the pubic arch and into contact with the shoulder of the baby, preferably conforming to the baby's anatomy, and then the arms of the device are manipulated, e.g., opened to a more spread position, rotated and/or pivoted. Once manipulated, the surgeon applies a downward force on the arms of the device causing the shoulder contacting (engaging) material of the device to atruamatically press against the baby's shoulder, thereby releasing the shoulder from the pubic arch so the baby can be safely delivered.

Turning now to the first embodiment of the device and with initial reference to FIG. 1, the device is designated generally by reference numeral 10 and includes a first arm 20, a second arm 40 and an engagement member 60 spanning the two arms 20, 40. Arms 20 and 40 in a preferred embodiment are substantially identical, although they could be varied from each other as long as their function as described herein is maintained. Arm 20, as shown in FIGS. 1 and 4, has a grasping handle 22, a substantially straight or substantially linear arm portion 24, a first curve 26, a curved portion 28, and a second curve 30 terminating in a distal tip 32. The arm 40 similarly has grasping handle 42, a substantially straight or substantially linear arm portion 44, a first curve 46, a curved portion 48, and a second curve 50 terminating in a distal tip 52. Each arm 20, 40 is curved to accommodate the natural curvature of the maternal pubic bone and symphysis pubis and the contours of the fetal shoulder. That is, as shown, the bottom portion of the arms 20 and 40 (as viewed in the orientation of FIG. 1) has a somewhat S-shaped curve. The distal tips 32, 52 are preferably round to provide an atraumatic blunt end. The arms can be composed of a metal or plastic material.

Note as used herein the term "distal" denotes the portion or section of the device further from the user and the term "proximal" denotes the portion or section of the device closer to the user.

The grasping handles 22 and 42 preferably have solid surfaces 23, 43, respectively, for engagement by the surgeon's thumbs to provide leverage for a downward movement of the device 10 as described below in conjunction with the method or use. The grasping handles 22 and 42 can alternatively be grasped by other fingers or held in the palm of the surgeon's hand as alternate ways to provide the appropriate leverage to apply the necessary force to dislodge the baby's shoulder from engagement with the pubic arch as described below. The grasping handles 22, 42 can be composed of a metal or plastic material.

An engagement component or section of the device is designated by reference numeral 60 and spans a distal region between the two arms 20, 40. The space between the two arms preferably ranges from about 4 cm to about 10 cm, and preferably between about 5 cm and about 8 cm, although other distances are also contemplated. The engagement section in the open (unfolded) position preferably has a length of about 8 cm to about 12 cm and a width of about 4 cm to about 10 cm, and preferably between about 5 cm and 8 cm, although other dimensions are also contemplated. The engagement section 60 includes a proximal section 62 and a distal section 64. The proximal section 62 is preferably more flexible, i.e., has greater elasticity, to conform to the baby's shoulder. The distal section 64 is preferably more rigid, and in some embodiments can be non-elastic, to apply a sufficient force against the baby's shoulder when a downward force is applied by manipulation of the arms 20, 40. As shown, preferably the proximal section 62 occupies less than 50 percent of the total engagement section area, although it could occupy more or less of the total engagement section area.

In one embodiment, the engagement section 60 comprises a material in the form of a sheet or a cloth. The distal section 64 of the sheet or cloth can have a reinforcement harder material attached thereto or positioned therein to rigidify the distal section. In other embodiments, two separate materials (or materials of differing hardness) form the engagement component, with the material forming the distal section more rigid and the material forming the proximal section more flexible and stretchable. The two sections 62, 64 of different materials can be attached by various known methods such as being sewed together. Various materials can be utilized to achieve the part flexible/part rigid feature of the engagement component 60. The less elastic material or section strikes the optimal balance of rigidity to apply a sufficient force to move the baby's shoulder while being sufficiently atraumatic to avoid maternal or baby injury. It is also contemplated that instead of cloth, plastic material of different elasticity can also be utilized to achieve the same objective of a more rigid distal region. The less elastic or non-elastic distal region provides a strong surface for manipulation of the baby in the methods described below.

In an alternate embodiment, the engagement section or component can be of the same material but formed in a substantially trapezoidal shape. This substantially trapezoidal shape can be similar to that shown in the alternate embodiment of FIG. 19 described in detail below. With a substantially trapezoidal shaped engagement material, the differing rigidity can be achieved with the same material. That is, the shape of the material can provide a more rigid and less stretchable distal section. Note that the substantially trapezoidal shape can also be used if different materials are provided for the engagement section.

More specifically, if a substantially trapezoidal shape such as that shown in FIG. 19 is used with the arms of the embodiments of FIG. 1 or FIG. 9, the stiffer distal section is a result of the shape. That is, the base of the trapezoidal shape is at a proximal section and the side opposite the base (the distal side) has a shorter length. As a result, when the arms are moved from the closed (unspread) to the open spread position, due to the shorter length distal end, the distal section of the engagement section will be more taut, and thus more rigid, than the proximal section to achieve the results described above. Note it is also contemplated that the various materials, stiffnesses, etc. described above can also be configured in the substantially trapezoidal shape of FIG. 19. Note FIGS. 21-23 show an alternate use of the device utilizing the substantially trapezoidal material.

Turning back to the embodiment of FIG. 1, the upper (top) surface 66 of the engagement component 60 can be smooth to provide a non-abrasive surface, thereby preventing abrasion of the maternal tissue. A portion of the lower (bottom) surface 68 (see FIG. 3A) (or the entire lower surface) can be textured or have some small atraumatic projections or other non-smooth surface to provide a good grip on the fetal shoulder for maneuverability. An example of a non-smooth lower surface is shown in FIG. 3B where engagement section 60' has projections 61 formed on its lower surface 68'. In all other respect, the device of FIG. 3B is the same as the device of FIG. 3A. This non-smooth lower surface of the engagement section can be used with any of the embodiments described herein.

The engagement component 60 can be attached to the arms 20, 40 in various ways. In one version, pockets can be formed in the material 60 to receive the arms 20, 40 and then the pockets sealed around the arms 20, 40 such as by suturing. In an alternate embodiment shown in FIG. 5, holes 21 can be drilled in a distal region of the arm 20' (and in the opposing arm, not shown) and attached via screws or other fasteners that will preferably remain flush with the outer surface of the arms so as not to protrude and form an abrasive or traumatic surface with the maternal or fetal tissues. Sutures can also be passed through the holes 21 to suture the material 60 to the arms. Other methods to secure the connecting (engagement) material, e.g., connecting sheets, to the arms are also contemplated so long as they provide a strong attachment and do not create bulk effect that might lead to injury of the maternal or fetal tissues. Note holes can also be provided in the arms of the other embodiments disclosed herein to secure the engagement material.

Each arm 20, 40 is preferably made of a rigid non bendable material, such as stainless steel, although other materials are also contemplated. The outer diameter can be constant or of varying diameters along various regions of its length. For example, the exposed linear portions 24 and 44 can have a larger diameter than the curved portions 28, 48 which are inserted into the body. By minimizing the size, a reduced profile is achieved to enable insertion into the limited space in the pelvis. In preferred embodiments, the outer diameter of the linear portions is about 3 mm, although other dimensions are also contemplated.

In the alternate embodiment of FIGS. 9 and 10, a single curve is provided. The device is identical to the device of FIG. 1 except for the shape of the arms and therefore only one arm is shown, it being understood that a second arm identical or substantially similar to arm 80 would be provided. The two arms are joined at the distal section by an engagement component such as component 60, or any of the engagement component variations discussed above, and in any of the manners described above. The difference between arm 80 (and the second arm as well) and arm 20 is that instead of each arm having two curves like arm 20, arm 80 (and the second arm as well) has only the first curve. More specifically, arm 80 (and the second arm as well) has a substantially straight or linear arm portion 84 extending from handle 82, a curve 86, a curved portion 88, and a substantially straight or substantially linear portion 90 terminating in a blunt atraumatic distal tip 92. Thus, instead of a second curve like curve 30 of arm 20, this region of arm 80 is substantially straight. Consequently, in this embodiment, the curve 86 would conform to the contour of the baby's neck, and the lower aspect of the pubic bone, but the substantially linear portion 90 would not conform to the contour of the baby's shoulder as does curved portion 30 of arm 20 which conforms to this anatomy. However, once in position, the arms would be opened in the same manner as in the embodiment of FIG. 1, and the handles manipulated in the same manner as in FIG. 1, to press the engagement component against the baby's shoulder to provide a force in a direction away from the pubic arch to release the baby's shoulder. The device of FIGS. 9 and 10 can be inserted in the same manner as in FIG. 14 or 15, i.e., starting along the back and then moved to along the shoulder, or alternatively, due to the single curve, can be initially inserted over the fetal shoulder and under the pubic bone. Grasping handle 82 is the same as handle 22 of the device of FIG. 1, with a solid portion 83, and designed to be pressed by the surgeon to exert a force on the engagement component. The second arm also has a grasping handle like handle 82. This straighter arm version of FIG. 9, in some applications, can be easier to slide into the pelvic area under the pubic arch. Also, this straighter arch version can better accommodate different pelvic shapes in certain applications.

FIGS. 3C and 3D illustrate alternate embodiments of the engagement section to help push the engagement section over the baby's shoulder in certain applications. In FIG. 3C, engagement section 260 has a reinforcement strip 262 made of a stiffer (less flexible) material to provide more rigidity. The surgeon can with his finger push on the reinforcement strip 262 to advance the engagement section 260 over the baby's shoulder. The reinforcement strip 362 can be embedded in the engagement section material, or alternatively positioned on an upper surface or lower surface, or both surfaces. As shown, a single reinforcement strip 362 is positioned in the center, substantially parallel to handles of the device, although it can be placed in other regions and more than one reinforcement strip can be provided. In some embodiments, the reinforcement strip is made of a plastic material. In all other respects, engagement section 260 is identical to engagement section 60 (or engagement section 160 if formed into a trapezoidal shape).

In the embodiment of FIG. 3D, engagement section 360 has a plurality of pockets 362, formed therein, or attached thereto, which have openings 364 to receive an instrument such as a Kelly clamp. The clamp (not shown) can be inserted through the pocket opening(s) 364 and inserted with the device to help move the engagement section 360 over the baby's shoulder. The pockets can be formed on a top or a bottom surface (or both surfaces) of the engagement section 360. Alternatively, a single pocket with an elongated opening can be formed or attached to the engagement section to receive an instrument to aid insertion of the engagement section.

Turning now to the method of use, and with reference to FIGS. 11-18 which show the method using the device of the embodiment of FIG. 1 (or FIG. 3B or FIG. 5), FIGS. 11 and 12 show the baby's shoulder engaged with the pubic arch P of the mother and thereby blocking delivery of the baby in an incidence of shoulder dystocia. To address this case of shoulder dystocia, the surgeon inserts the device 10 of FIG. 1 with the arms 20 and 40, and therefore the engagement component 60, in the unopened (unspread) position as shown in FIG. 13. In this unopened (closed) position of the arms 20, 40, engagement section 60 is collapsed or folded as shown. The device 10 is initially inserted along the side of the baby's head and along the baby's back as shown in FIG. 14. Then, with the arms 20, 40 still in the closed position, the device 10 is maneuvered so the engagement section in the closed position rests against the baby's shoulder as shown in FIG. 15. Note that the curvature of the device arms substantially conforms to the neck and shoulder of the baby.

Next, the surgeon separates the grasping handles 22, 42 to spread the engagement section 60 from the closed position to the open spread position as shown in FIG. 16, thereby enveloping a portion of the baby's shoulder. Then, the surgeon presses down on grasping handles 22, 42, utilizing solid surfaces 23, 24 of grasping handles 22, 42 for leverage, to pivot the proximal portion of the arms 20, 40 downwardly as shown in phantom in FIG. 17 to force engagement section 60 downwardly. This force pushes the baby away from the pubic arch, thereby freeing the baby's shoulder from the pubic arch for delivery of the baby as shown in FIG. 18. Thus, the baby's shoulder is released from the arch in a quick and atruamatic fashion. In certain applications, in addition to the downward force, the handles 22, 42 can be rotated to the side (toward the fetal chest) to move the baby's shoulder to an oblique diameter of the pelvis. That is, such pivoting movement of the handles 22. 42 can rotate the baby, e.g., rotate the baby's shoulder, about 45 degrees, gaining two advantages: 1) the anterior shoulder is not hindered by the pubic arch; and 2) the oblique diameter of the pelvic outlet is larger than the anterior-posterior diameter of the mother, and therefore it is easier for the baby to come out through this position aided by pushing of the mother.

In an alternative insertion method, the device 10 (or any of the other devices disclosed herein) can be inserted below the posterior shoulder of the baby and then manipulated to rotate the baby to an oblique diameter of the pelvis.

The device of FIGS. 9 and 10 can be inserted and used in the same manner as in FIGS. 11-18, i.e., starting along the back of the baby and then moved to along the shoulder, with the curve 88 of arm 80 and the corresponding curve of the other arm substantially conforming to the neck of the baby. Alternatively, due to the single curve, the arms can initially be inserted directly under the pubic arch with one arm along the baby's back and the other arm along the baby's chest.

The shoulder engagement component is opened by movement of the arms apart and is then pushed against the shoulder and under the pubic arch to force the baby away from the pubic arch to free the baby's shoulder. This device can also be used to move the baby's shoulder to an oblique diameter of the pelvis in the same manner as described above in an alternate method of use.

The grasping handles of the device of FIG. 9 would be used in the same manner as handles 22, 42, with a solid portion aiding the downward force on the handles and thus on the shoulder engagement component to push the baby away from the pubic arch. The handles can also be rotated to move the baby's shoulder to the side as described above.

FIGS. 19 and 20 illustrate an alternate embodiment of the device of the present invention. In this embodiment, a single curve of the arms is provided as in the embodiment of FIGS. 9 and 10, however, this version has a different shaped engagement section. Note the arms of FIGS. 19 and 20 could alternatively have the double curve as in the embodiment of FIG. 1.

More specifically, the device, designated generally by reference numeral 100, has first and second arms 110, 130. Arms 110, 130 are joined at the distal section by an engagement component or section 160. Arm 110 has a substantially straight or substantially linear arm portion 114, a curve 116, a curved portion 118, and a substantially linear portion 120 terminating in a blunt distal tip 122. Thus, instead of a second curve like curve 30 of arm 20 of FIG. 1, this section of arm 110 is substantially straight. Arm 130 has a substantially straight or substantially linear arm portion 134, a curve 136, a curved portion 138, and a substantially linear portion 140 terminating in a blunt distal tip 142. Thus, instead of a second curve like curve 50 of arm 40 of FIG. 1, this section of arm 130 is substantially straight. In this embodiment, the curves 116, 136 substantially conform to the contour of the baby's neck and the lower aspect of the symphysis pubis, and the substantially linear portion extends along the baby's shoulder. The grasping handles 112, 132, with solid portions 113, 133, similar to solid portions 23, 43, are manipulated in the same manner as in FIG. 1, i.e., to press the engagement component (section) 160 against the baby's shoulder to provide a force in a direction away from the pubic arch to release the baby's shoulder from the arch and/or to allow it to move the baby to the oblique diameter to allow delivery. This straighter version, in some applications, can be easier to slide into the pelvis. This version can also better accommodate different pelvic shapes in certain applications.

The engagement section or component 160 is substantially trapezoidal in shape, having a proximal section 162 and a distal section 164, wherein the proximal section 162 has a width w1 (FIG. 20) greater than the width w2 of the distal section 164. In this manner, the varying tautness of the material of engagement section 60 is "built into" the device 100. Note the material can be a cloth or any other suitable material(s) as described herein with respect to the other embodiments to provide sufficient force to move the baby's shoulder while being atraumatic to surrounding tissue. In this embodiment of FIGS. 19 and 20, due to the short width w2 in the distal section, the material will be held more rigid than in the proximal section 162 when the handles are moved apart. In one embodiment, the distal edge 165 of the engagement section 160 is about 3 cm and the proximal edge 167 is about 6 cm, with the distance between the two edges being about 10 cm. Other dimensions are also contemplated.

As shown in FIG. 20, the two arms 110, 130 are angled toward each other to accommodate the substantially trapezoidal shaped material 160. During use, the arms 110, 130 are manipulated away from each, i.e., toward a parallel position, thereby tightening the distal section 164. For example, in one embodiment, the distal edge 165 can be stretched from about 3 cm to about 6 cm when the arms 110, 130 are moved to a substantially parallel position, with the proximal edge 167 not changing width. This results in the proximal section 162 remaining more flexible/stretchable to comfortably stretch over the baby's shoulder while the distal section 164 is more rigid to apply sufficient force to move the baby. Stretching the distal edge 165 to different dimensions is also contemplated. It is also contemplated that the proximal edge 167 can be slightly stretched when the arms 110, 130 are moved away from each other to stretch the distal edge 165, except not to the same extent, to obtain the rigidity of the distal section while maintaining the flexibility of the proximal section.

Note this substantially trapezoidal shape could also be used with the arms of FIGS. 1 and 5.

Turning to FIGS. 21-23, the method of use of the device 100 of FIGS. 19 and 20 will now be described. As shown in FIG. 21, the device 100 is in its initial position with arms 110, 130 angled toward each other as shown grasped by the physician. The material (engagement section) 160 is not folded or collapsed as in the embodiment of FIG. 1, thereby providing a lower profile for insertion. The device 100 is inserted from the center, sliding the distal edge of the material 60 under the pubic arch P and over the fetal shoulder as shown in FIGS. 22 and 23. Then, each arm 110, 130 is turned slightly to the side i.e., moved away from each other, so the distal ends are moved away from each, moving the arms 110, 130 toward a more parallel position, thereby stretching the distal section 164 of the material (engagement section) 160 as described above. Since the proximal edge 167 does not change its length, or not substantially change its length, the proximal section 162 is more stretchable and can comfortably stretch over the fetal shoulder while the distal section 164 becomes more rigid. Once the arms 110, 130 are moved apart, the surgeon can then press down on the handles 112, 132 of the arms 110, 130 in the same manner as in FIGS. 17 and 18 described above so distal section 164 presses down on the baby's shoulder to free the baby's shoulder from the arch P to deliver the baby. The surgeon can also rotate the handles 112, 132 to the side to move the baby's shoulder to the side to an oblique diameter of the pelvis as described above.

Note that the device 100 of FIGS. 19 and 20 can also be initially inserted in the same manner as in FIG. 14, i.e., from the baby's back and then moved to the baby's side as in FIG. 15, or alternatively under the posterior shoulder. Also, it is contemplated in alternate embodiments the arms 110, 130 can be closer together and the engagement section 160 folded for insertion.

It should be noted that both arms, whether having the double curve as in the embodiment of FIG. 1 or the single curve as in the embodiment of FIG. 9 or FIG. 19, can have a mechanism that will allow articulation with respect to one another and thus manipulation by the operator with one hand only.

The devices disclosed herein have several qualities that allow it to resolve the shoulder dystocia quickly and safely:
1. A unique structure that allows it to negotiate the tight "S" shaped contact area between the fetal shoulder and neck and the aspects of the maternal pubic arch.
2. The device applies pressure over large areas of the fetal body, specifically to the cranial aspect of the humerus and the shoulder joint, thus avoiding pressure points and minimizing the risk of fractures or soft tissue injuries.
3. The device does not apply pressure to the maternal tissues, and does not use parts of the maternal anatomy as fulcrum points, thus minimizing the risk of maternal injury.
4. The device allows the operator a good grip of the fetal shoulder girdle, thus allowing the operator to rotate the fetal torso with ease.
5. The application of the device uses both of the operator's hands, each one manipulating another arm of the device. Thus it prevents the instinctive traction that the operator wants to apply to the fetal head until after the fetal shoulder is removed from behind the pubic arch. That is, under the emergency conditions of shoulder dystocia, health providers might underestimate the force that they apply to the fetal head and the intensity of the traction can injure the fetus, especially through damage to the brachial plexus.

The devices disclosed herein can be composed of disposable materials or reusable sterilizable materials.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical device for treating shoulder dystocia comprising:
   a first arm having a proximal portion and a distal portion, the first arm having a first curved surface;
   a second arm having a proximal portion and a distal portion, the second arm having a second curved surface; and
   a shoulder engagement section positioned at least between the distal portion of the first and second arms and connecting the first and second arms, the engagement section having an atraumatic surface and configured to contact and press down on a baby to reposition the baby upon arm manipulation, wherein the engagement section includes a first section and a second section, wherein the second section is contiguous with the first section at a central portion and the second section is more flexible than the first section, the second section positioned proximal of the first section.

2. The device of claim 1, wherein the first and second sections are composed of the same material.

3. The device of claim 1, wherein the first and second sections are composed of a different material.

4. The device of claim 1, wherein the first section has a first width less than a second width of the second section of the engagement section, the first and second widths defined by a distance from the first arm to the second arm.

5. The device of claim 4, wherein the engagement section is substantially trapezoidal in shape.

6. The device of claim 1, wherein the first and second arms each have handle portions, the handle portions being manipulable independently.

7. The device of claim 1, wherein the first arm includes a third curved surface distal of the first curved surface and the second arm includes a fourth curved surface distal of the second curved surface, the third and fourth curved surfaces providing a curved distal end of the first and second arms.

8. The device of claim 1, wherein a lower surface of the engagement section has a non-smooth surface to enhance gripping.

9. The device of claim 1, wherein the first and second arms are movable from a first position to a second more spread position to move the engagement section to a more spread position.

10. The device of claim 1, wherein an upper surface of the engagement section has a non-abrasive surface to prevent abrasion of maternal tissue.

11. A surgical device for treating shoulder dystocia by moving a baby away from a maternal pubic arch to free a shoulder of the baby to allow delivery, the device comprising:
    a first arm having a proximal portion, a distal portion, and an intermediate portion between the proximal portion and the distal portion, the proximal portion extending proximally from the intermediate portion, the first arm having a first curved surface and configured to be inserted between the baby and the pubic arch, the distal portion of the first arm extending outwardly with respect to a longitudinal axis of the intermediate portion of the first arm;
    a second arm having a proximal portion, a distal portion, and an intermediate portion between the proximal portion and the distal portion, the proximal portion extending proximally from the intermediate portion, the second arm having a second curved surface and configured to be inserted between a baby and the pubic arch, the distal portion of the second arm extending laterally outwardly with respect a longitudinal axis of the intermediate portion of the second arm; and
    a shoulder engagement section positioned at least between a distal region of the first and second arms and connected to the first and second arms, the shoulder engagement section having an upper surface facing proximally and a lower surface facing distally, the engagement section configured for insertion between the baby and the pubic arch, the lower surface of the engagement section having an atraumatic surface for contacting the baby and configured to contact and press down on a shoulder or chest of the baby to move the baby downwardly away from the pubic arch to free the baby's shoulder from the pubic arch to enable delivery of the baby, wherein such downward pressure by the engagement section is effected by downward movement of the arms.

12. The device of claim 11, wherein a distal section of the engagement section is less flexible than a proximal section of the engagement section.

13. The device of claim 11, wherein the engagement section has a first width at a distal section and a second width at a proximal section, wherein the first width is less than the second width to thereby provide a less flexible distal section, the first and second widths defined by a distance from the first arm to the second arm when the first and second arms are spaced apart.

14. A surgical device for treating shoulder dystocia comprising:
    a first arm having a proximal portion, a distal portion, and an intermediate portion, the distal portion having a curved region, and an end region and the curved region extending at an angle to the intermediate portion;
    a second arm having a proximal portion, a distal portion and an intermediate portion, the distal portion and having a curved region and an end region, and the curved region extending at an angle to the intermediate portion; and a shoulder engagement section extending between at least the distal portion of the first and second arms, the engagement section extending along a length of the distal portion to provide a contiguous region such that a distal edge of the engagement section is at the end region of the first arm and a proximal edge of the engagement section is at the curved region of the first arm, the engagement section having an atraumatic surface and configured to be inserted beyond a head and neck of a baby to contact and press down on the baby at a region below the neck of the baby to reposition the baby upon manipulation of the first and second arms.

15. The device of claim 14, wherein the first arm has a first curved surface and the second arm has a second curved surface.

16. The device of claim 14, wherein the distal portion of the first arm extends transversely to a more proximal region of the first arm and the distal portion of the second arm extends transversely to a more proximal region of the second arm.

17. The device of claim 14, wherein the arms are independently manipulable.

18. The device of claim 14, wherein the first and second arms are movable from a first position to a second more spread position to move the engagement section to a more spread position.

* * * * *